United States Patent [19]

Paxton

[11] Patent Number: 4,815,315

[45] Date of Patent: Mar. 28, 1989

[54] PROCESS FOR ASSESSING THE EFFECT OF PROPELLANT STRAIN ON PROPELLANT BURN RATE

[75] Inventor: Ronald B. Paxton, Brigham City, Utah

[73] Assignee: The United States of America as represented by the Secretary of the Air Force, Washington, D.C.

[21] Appl. No.: 107,184

[22] Filed: Oct. 13, 1987

[51] Int. Cl.$^4$ ............................................. G01N 33/22
[52] U.S. Cl. ........................................... 73/35; 73/116
[58] Field of Search ...................................... 73/35, 116

[56] References Cited

U.S. PATENT DOCUMENTS 4,409,821  10/1983  Battles et al. ........................ 73/116
4,554,823  11/1985  Lilley ..................................... 73/35

Primary Examiner—John Chapman
Attorney, Agent, or Firm—Stanton E. Collier; Donald J. Singer

[57] ABSTRACT

The present invention describes a process for relating burn rate in a sample propellant to a strain field imposed therein by bending the sample propellant by a determined amount. The propellant is cast upon an initially flat plate having a single pair of fixed parallel walls. The plate is bent parallel to the walls before the test burn. Measurements of the thickness of the propellant before the burn and after the burn are related to the strain placed in the propellant by the bending. All measurements occur when the plate is flat.

4 Claims, 1 Drawing Sheet

PROCESS FOR ASSESSING THE EFFECT OF PROPELLANT STRAIN ON PROPELLANT BURN RATE

STATEMENT OF GOVERNMENT INTEREST

The invention described herein may be manufactured and used by or for the Government for governmental purposes without the payment of any royalty thereon.

BACKGROUND OF THE INVENTION

The present invention relates to rocket propellants, and, in particular, relates to a process of determining how strain in the cured propellant affects the burn rate.

The previous process for determining how strain in a cured propellant affected the burn rate used a cylindrical sample being essential shaped like the rocket motor. Because of the curing process and thermal shrinkage, strain is developed in the rocket motor propellant. The strain is biaxial in nature in that it is parallel to the longitudinal axis of the rocket motor and transverse thereto. A pressure versus time trace of the burn with an assumed burn distance provides an approximate measure of the burn distance. The actual distance is normally difficult to measure in a test burn because of additional variables that obscure the effect of strain on the burn rate.

This inability to measure burn rate as a function of strain has motivated a search for a process that is able to accomplish such a task.

SUMMARY OF THE INVENTION

The present invention is directed at a process of testing a sample propellant under a given strain to determine the effect of burn rate as a function of the strain.

A text fixture for holding the sample propellant has a flat base of metal with two parallel spaced-apart walls perpendicular to the base. The base is bendable along an axis parallel to the walls and approximately midway therebetween.

The sample propellant is poured into a rectangular open topped box formed when two additional temporary parallel walls are added to the base and are perpendicular to the other walls to form the open topped box. After the propellant is cured the temporary walls are removed leaving a rectangularly shaped mass of propellant on the base having two walls thereabout.

Before bending, the thickness of the sample propellant plus base is determined at various points over the surface. The base is then bent to establish a strain field in the sample propellant.

The sample propellant is ignited and allowed to burn for a short period of time so as not to burn to the base metal.

The base is then straightened and again thickness measurements are taken at the previous measuring points. Any variations in thickness are related to the strain in the sample propellant since other variables can be minimized in this process.

It is therefore one object of the present invention to provide a process for determining the effect of propellant strain on propellant burn rate.

It is another object of the present invention to provide a process of testing propellant specimens wherein uncontrolled variables are eliminated to the maximum extent.

It is another object of the present invention to provide a process that approximates the motor strain field and direction of burn relative to the strain.

It is another object of the present invention to provide a process that simplifies use and testing.

These and many other objects and advantages of the present invention will be readily apparent to one skilled in the pertinent art from the following detailed description of a preferred embodiment of the invention and the related drawings.

DETAILED DESCRIPTION OF THE PREFERRED EMBODIMENT

Figure 1:
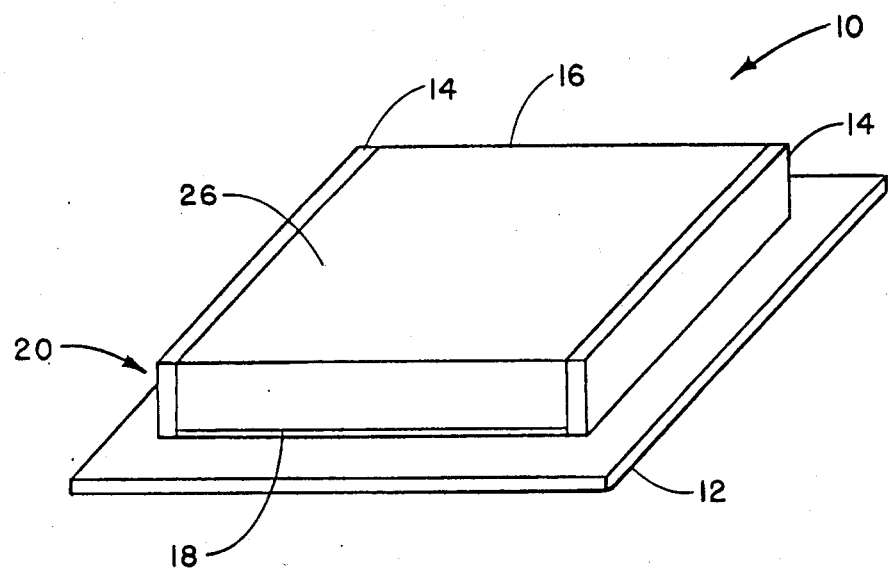
FIG. 1 illustrates by view the test fixture with propellant therein.

Referring to FIG. 1, a test specimen 10 is shown for the process of the present invention. Test specimen 10 includes a base plate 12 of metal with a pair of parallel, spaced-apart walls 14 for holding a cured sample propellant 16. An added feature is an interface 18 placed between sample propellant 16 and plate 12. Interface 18 may be like a rocket motor liner.

Figure 2:
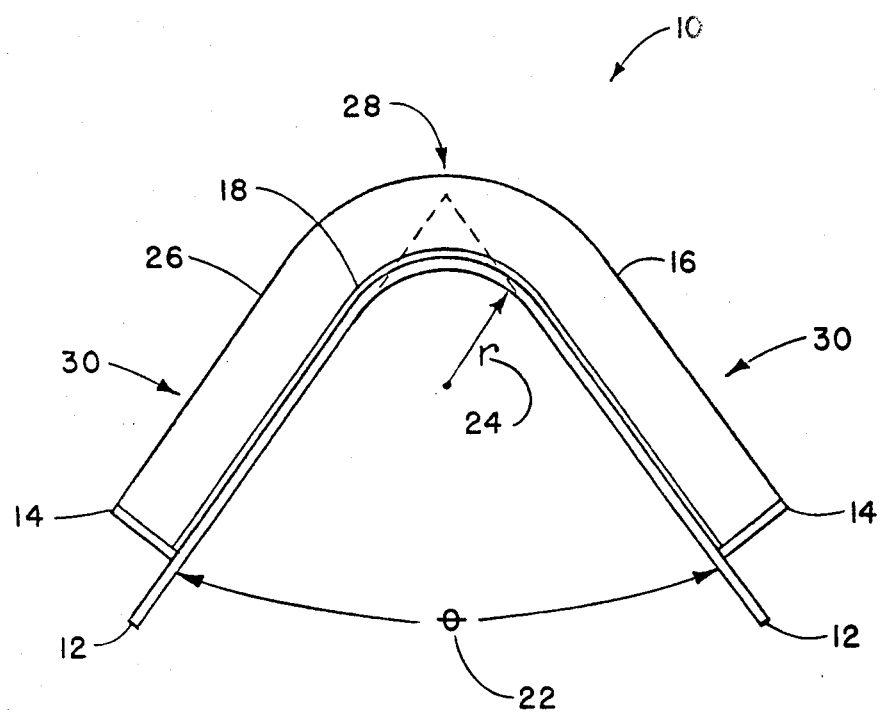
FIG. 2 illustrates by side view the test fixture with propellant therein bent to provide a strain field.

A test fixture 20 for holding sample propellant 16 includes base 12 and walls 14 without sample propellant 16 therein. A plurality of fixtures 20 having the same dimensions eliminate these types of variables as a result since each fixture 20 can be compared to the next. Base plate 12 is typically made of a metal such as steel or aluminum but other metals are acceptable as long as they are easily bendable. The plate may be about 12 inches square. Referring to FIG. 2, plate 12 must be bendable to an angle θ, 22, and thus the thickness of plate 12 must be such as to allow this bending. The radius r, 24, of the bend can be selected by bending the plate 12 over a rod, not shown, having a radius r, 24. The amount of bend as defined by angle θ, 22, and radius r, 24, determines the strain field that will exist in propellant 16. Actual measurements by strain gauges, for example, determines the strain field.

Walls 14 are rigidly attached to plate 12 by welding or screws and are approximately one inch in height, 90 degrees from plate 12, and parallel to each other. Temporary walls perpendicular to walls 14, now shown, are used to contain fluid-like propellant 16 before curing.

Propellant 16 has a top surface 26 that may be molded or cast like a motor propellant. Propellant 16 can be pressure cured. Surface 16 need not be flat but other configurations may complicate measurement of burn depth. Proellant 16 may have a dimension of about 8 inches to assure a biaxial strain field at the center. After curing, test specimen 10 as seen in FIG. 2 is bent to a predetermined angle θ, 22, with a radius r, 24, bend. The amount of strain is controlled by θ, 22, and r, 24.

As seen in FIG. 2, as a result of bending a high strain level 28 exists at the bend and a low strain level 30 exists near walls 14. The strain level is determined by analysis and/or strain gauges. Before the bending, the thickness of propellant 16 and plate 12 are measured at various points.

Test specimen 10 is ignited and then quenched before the burn reaches plate 12. Then fired test specimen 10 is straightened out as best as possible without damage to propellant 16 and again the thickness at various points is measured. The differences in the thicknesses are then a direct result of the strain. The amount, if any, of burn rate augmentation is due to strain and is thus determined by measurement differences between the center and the ends of test specimen 10.

The benefits of this process are clear and are as follows: (1) the same test fixture 20 can be used for several strain levels by adjustment of $\theta$, 22, and/or r, 24; (2) the test specimen 10 approximates the motor strain fields and direction of burn relative to the strain; (3) different levels of strain occur in the same sample; (4) burn distances are easily measured after the sample is bent back; and (5) initial surface strain levels can be obtained by strain gauges.

Clearly, many modifications and variations of the present invention are possible in light of the above teachings and it is therefore understood, that within the inventive scope of the inventive concept, the invention may be practices othewise than specifically claimed.

What is claimed is:

1. A process for testing rocket propellant burn rate as a function of strain, said process comprising the steps of:
   a. providing a test fixture having a means of holding a sample propellant therein and being bendable in a desired manner;
   b. curing said sample propellant within said test fixture to provide a test specimen for said process;
   c. measuring the thickness of said sample propellant at a plurality of locations;
   d. bending the sample propellant in a desired manner to produce a strain field therein;
   e. determining the strain in the strain field;
   f. igniting said sample propellant;
   g. quenching the burning sample propellant before the sample propellant burns through to said test fixture;
   h. straightening the bend as produced by step "d";
   i. measuring the thickness of said sample propellant at said various locations;
   j. comparing the different thicknesses in steps "c" and "i" to determine differences at each location; and
   k. relating the depth of burn at said various locations with a value of strain thereat.

2. A process as defined in claim 1, wherein said test fixture has a base plate with two parallel, spaced-apart walls thereon, said fixture being bendable about an axis parallel to said walls and about midway therebetween to effect said bending of said sample propellant.

3. A process for testing rocket propellant burn rate as a function of strain, said process comprising the steps of:
   a. providing a test fixture having a means of holding a sample propellant therein and being bendable in a desired manner;
   b. curing said sample propellant within said test fixture to provide a test specimen for said process;
   c. measuring the thickness of said sample propellant at a plurality of locations;
   d. bending the sample propellant in a desired manner to produce a strain field therein, aid bending causing a bend of a given radius and given angle about said bend to occur;
   e. determining the strain in the strain field;
   f. igniting said sample propellant;
   g. quenching the burning sample propellant before the sample propellant burns through to said test fixture;
   h. straightening the bend as produced by step "d"
   i. measuring the thickness of said sample propellant at said various locations;
   j. comparing the different thicknesses in steps "c" and "i" to determine differences at each location; and
   k. relating the depth of burn at said various locations with a value of strain thereat.

4. A test fixture for determining burn rate of a cured sample propellant as a function of strain in the sample propellant, said test fixture comprising:
   a base plate, said base plate being essentially flat and bendable about an axis; and
   a single pair of parallel, spaced apart walls, said walls affixed to said base plate in a perpendicular manner and containing said sample propellant therebetween.

* * * * *